United States Patent [19]

Goldsmith

[11] 4,199,003
[45] Apr. 22, 1980

[54] FLOW CONTROL SYSTEM WITH DENSITY COMPENSATION

[75] Inventor: James S. Goldsmith, Cincinnati, Ohio

[73] Assignee: The United States of America as represented by the Secretary of the Navy, Washington, D.C.

[21] Appl. No.: 969,901

[22] Filed: Dec. 15, 1978

[51] Int. Cl.² ............................................. G05D 24/00
[52] U.S. Cl. ....................................... 137/467.5; 73/54
[58] Field of Search ...................... 137/467.5, 487.5, 4, 137/92; 73/54, 194 C, 229

[56] References Cited

U.S. PATENT DOCUMENTS

| | | | |
|---|---|---|---|
| 2,716,337 | 8/1955 | Fontein | 73/54 |
| 3,181,348 | 5/1965 | Lewis | 73/54 |
| 3,215,185 | 11/1965 | Black | 137/467.5 |
| 3,372,596 | 3/1968 | Keller | 73/194 C UX |
| 3,465,573 | 9/1969 | Shoemaker | 73/54 |

*Primary Examiner*—Alan Cohan
*Attorney, Agent, or Firm*—R. S. Sciascia; Henry Hansen

[57] ABSTRACT

Apparatus for continuously measuring and correcting for fuel density in an aircraft engine fuel metering system. Fuel, sampled at the inlet to the engine metering valve, is fed through a flow regulator to a vortex spin chamber in which the fuel is tangentially injected. A magnetic ball carried by the fuel in a race integral with the vortex chamber generates an electrical pulse in an electromagnetic coil at a frequency proportional to the tangential velocity of the fuel. The pulse frequency is compared to a reference frequency and the error signal modulates the regulator to maintain the tangential velocity constant. The radial static differential pressure of the chamber is directly proportional to the fuel density. This signal provides a compensating signal to the fuel metering valve for correcting the mass flow rate of the fuel based on a known true volumetric flow rate.

6 Claims, 2 Drawing Figures

FLOW CONTROL SYSTEM WITH DENSITY COMPENSATION

STATEMENT OF GOVERNMENT INTEREST

The invention described herein may be manufactured and used by or for the Government of the United States of America for governmental purposes without the payment of any royalities thereon or therefor.

BACKGROUND OF THE INVENTION

The present invention relates generally to apparatus for continuously measuring fluid density, and more particularly to apparatus for compensating a fluid metering system for variations in fluid density.

Aircraft engine fuel control systems have established and controlled volumetric fuel flow rates, but the mass flow rate is usually required to properly meter and control heat release in the engine combustors. The conversion of volumetric flow rate to mass flow rate in the control system has been predicated on the known density for a given fuel batch. It is well recognized, however, that the known density varies substantially in flight due to variations in fuel temperature. Fuel control systems have compensated for this variation by sensing the temperature and applying a corresponding correction, for example, to the reference setting of the volumetric metering valve. The temperature compensation is often accomplished with a bi-metallic spring but the compensation accuracy, with wide variations in fuel temperature, is limited by the linearity and repeatability of the temperature-to-spring force conversions. Furthermore, prior art systems offer no automatic compensation for density variations which occur between batches of the various hydrocarbon fuel types. Manual adjustment for these basic density variations among fuel types is typically provided in the metering control systems, and the proper reference setting is made by the crew prior to flight based on the fuel type used.

SUMMARY OF THE INVENTION

Accordingly, it is a general purpose and object of the invention to provide a novel apparatus which directly and continuously measures density changes of a fluid independent of the cause for the density variation. Another object of the invention is to provide apparatus for automatically compensating a fluid metering system for variations in density measuring apparatus in an aircraft engine fuel control system which is independent of engine speed. Still other objects are to provide a density measuring apparatus which is useful for a wide variety of liquids and gases, relatively inexpensive to manufacture and maintain, reliable and accurate, and which may be utilized in existing fluid control systems.

Briefly, these and other objects of the invention are accomplished by a fluid density compensator in a flow control system in which fluid sampled at the inlet to a metering valve is tangentially injected at a constant velocity into a fluidic vortex spin chamber and the radial static pressure differential in the chamber generates a density compensating signal to the metering valve. A steel ball carried around a race integral with the spin chamber at the tangential velocity generates a voltage pulse in an adjacent electromagnetic pick-up coil to provide a pulse frequency proportional to the tangential velocity. Compared to a reference frequency, the error signal regulates the fluid sample flow to the chamber to maintain the tangential velocity constant.

For a better understanding of these and other objects and aspects of the invention, reference may be made to the following detailed description taken in conjunction with the accompanying drawings wherein:

DESCRIPTION OF THE PREFERRED EMBODIMENT

Figure 1:
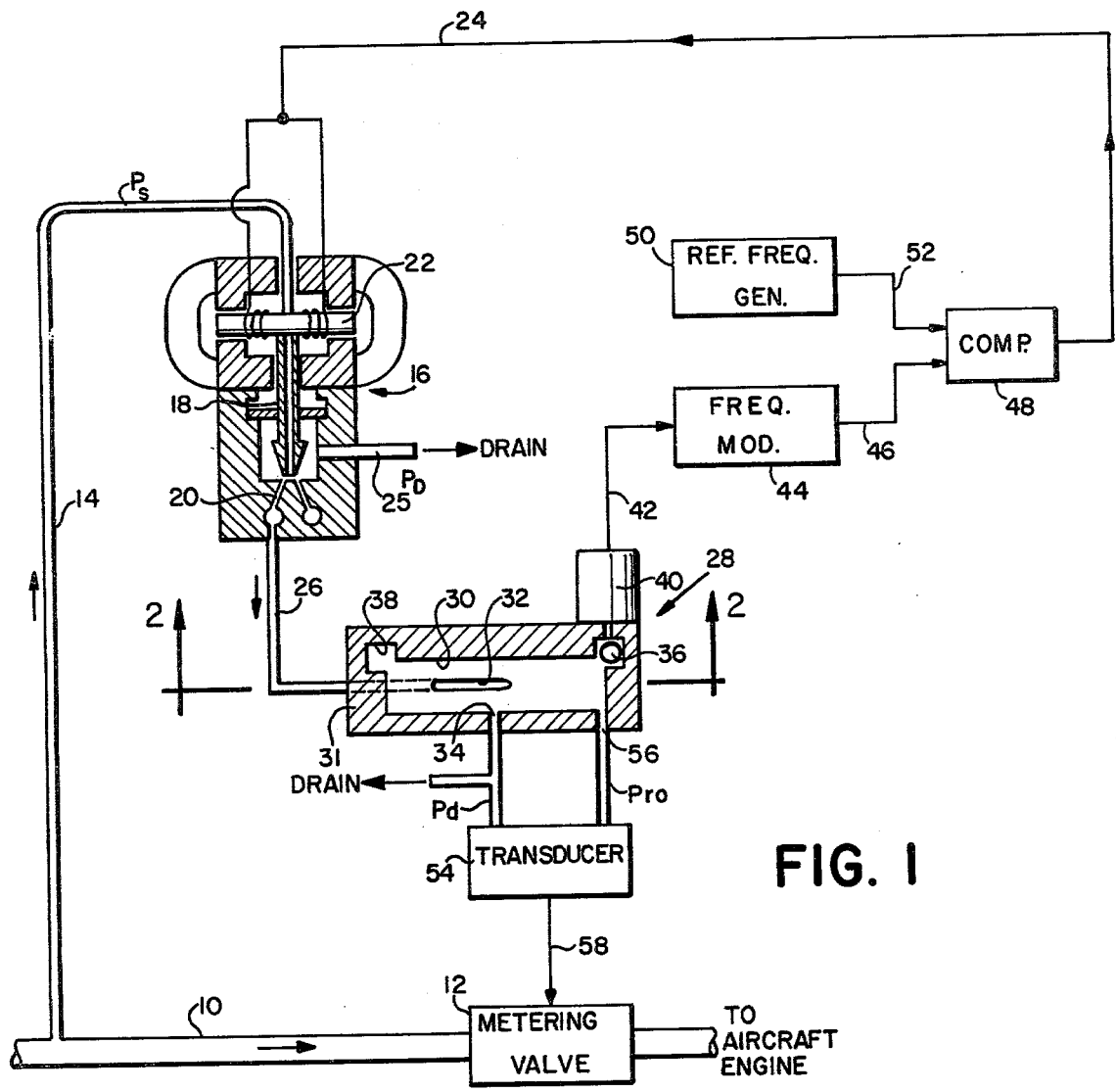
FIG. 1 is a schematic representation of a density compensator in an aircraft engine fuel control system according to the present invention.
Figure 2:
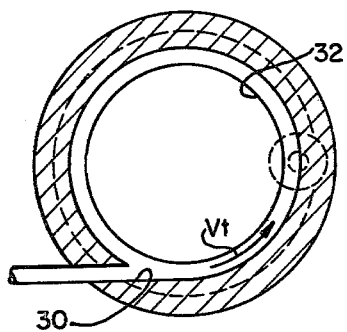
FIG. 2 is a transverse cross-sectional view of a vortex spin chamber according to the invention as shown in FIG. 1.

Referring now to the drawing wherein like characters designate like or corresponding parts throughout the several views, there is shown in FIG. 1 a pressurized fuel supply line 10 with a metering valve 12 for controlling the fuel to an aircraft engine, not shown. The valve 12 may be of a well known type responsive to command and engine and flight parameters. A fuel sample line 14 tapped into line 10 at the inlet of metering valve 12 connects the fuel sample at a static pressure $P_s$ to the inlet of a conventional jet pipe amplifier 16. The nozzle at a jet pipe 18 of the amplifier 16 movably registers with an orifice 20 to vary the flow rate at the outlet to line 26. A torque motor 22 fixed to jet pipe 18 moves the nozzle in response to an electrical input signal Y on conductor 24 to proportionally vary the flow rate in line 26. Excess fuel from jet pipe 18 is returned to the fuel tank via drain line 25.

The sampled fuel in line 26 is fed to a fluidic vortex spin unit 28 comprising a short cylindrical chamber 30 within a housing 31 of nonmagnetic material. The fuel is tangentially injected into chamber 28 at a side inlet slot 32 and axially discharged to a drain through an end outlet orifice 34 at an inner radius. A free vortex is thereby established in spin chamber 28 with a radial static pressure gradient which is a function of the fluid density, the tangential velocity, and the fixed geometry of the chamber. See "Experimental Profiles of Velocity Components and Radial Pressure Distributions in a Vortex Contained in a Short Cylindrical Chamber", J. M. Savino & E. G. Keshock, NASA, Lewis Research Center, Cleveland, Ohio, October 1965, NASA-TN-D3072. A radial static pressure differential in chamber 28 is expressed by $$P_{ro} - P_d = \frac{\gamma V_t^2 \left[ \left(\frac{ro}{r}\right)^{2n} - 1 \right]}{2gn}$$

where:
$P_{ro}$ = static pressure at chamber outer radius ro,
$P_d$ = static pressure at the outlet orifice radius r,
$\gamma$ = fluid weight density
$V_t$ = tangential injection velocity
n = a constant, not necessarily an integer,
ro = outer chamber radius,
r = outlet orifice radius, and
g = gravitational constant.

It is thusly apparent that if the tangential injection velocity $V_t$ is held constant, the static pressure differential $P_{ro} - P_d$ is directly proportional to fluid density.

In order to maintain the proportionality of density to static pressure differential, the tangential injection velocity $V_t$ must be measured and regulated. Measurement is provided through a small magnetic ball 36, preferably steel, contained in an annular race 38 continuously communicating along the circumference of chamber 30 at one end. Ball 36 is carried by the sample fuel around race 38 at an angular velocity corresponding to the tangential injection velocity $V_t$. Each revolution of ball 36 generates a voltage pulse in an electromagnetic pick-up coil 40 mounted on housing 31 adjacent to race 38 thus providing an electrical pulse on output 42 at a frequency proportional to the tangential injection velocity $V_t$. A frequency modulator 44 converts the detected pulses into a corresponding frequency at its output 46 suitable for frequency comparison in a comparator 48 with a fixed frequency reference output 52 from a generator 40. The difference or error signal on the output 24 of comparator 48 is operatively connected to torque motor 22 to position jet pipe 18 as described herein. In this manner, amplifier 16 regulates the fuel sample to vortex spin unit 28 at a constant tangential velocity $V_t$ irrespective of engine speed. The regulation occurs at any engine speed which will provide the fuel sample supply pressure $P_s$ sufficiently high for tangential velocity modulation required.

A differential static pressure transducer 54 connected to orifice 34 and an orifice 56 in one end of the chamber 30 at the outer radius produce a differential signal on output 58 proportional to the differential static pressure $P_{ro} - P_d$. Metering valve 12 is connected to receive the signal output 58 and thereby compensates the engine fuel demand for variations in fuel density.

Summarizing operation of the system, fuel to the aircraft engine metering valve 12 is sampled through jet pipe amplifier 16 to vortex spin 28. The tangential velocity of the vortex is maintained constant by regulating the flow to unit 28 according to the angular velocity of ball 38 as detected by coil 40 and comparator 48. The differential static pressure between the vortex discharge orifice and its periphery, as measured by transducer 54, produces an output signal indicative of the fuel density which modifies the metering valve 12 position accordingly.

Accordingly, some of the many advantages of the invention should now be readily apparent. Apparatus is provided which senses and measures variable fluid density such that the resulting automatic measurement can be utilized to continuously compute or correct mass flow rates of the sensed fluid based on known true volumetric flow rates. Manual adjustment of a specific gravity reference to compensate for changes in fuel batch or type is eliminated. The apparatus is particularly applicable to detection and correction for hydrocarbon fuel density change occurring in fuel flow rate metering controls used in aircraft jet propulsion engines. The apparatus, however, is not limited to aircraft jet engine fuel metering, since any flowing fluid, either liquid or gaseous, can operate the basic vortex spin unit which provides the mechanism of the measurement.

It will be understood that various changes in the details, steps and arrangement of parts, which have been herein described and illustrated in order to explain the nature of the invention, may be made by those skilled in the art within the principle and scope of the invention as expressed in the appended claims.

What is claimed is:

1. In a fluid metering system, an improved density compensator comprising, in combination:
   regulator means operatively connected to the system for continuously sampling a portion of the fluid to be metered;
   a non-magnetic housing forming a short cylindrical chamber and tangentially receiving the sampled fluid at an outer radius and axially discharging the fluid at an inner radius;
   an electromagnetic means operatively connected to said housing for producing an error signal indicative of change in the tangential velocity of the sampled fluid at the outer radius, said error signal controlling the amount of fluid sampled by said regulator means; and
   pressure differential means operatively connected to said housing for measuring the static pressure gradient at the inner and outer radii and producing an output signal to the metering system indicative of the fluid density.

2. A fluid density compensator according to claim 1 wherein said electromagnetic means further comprises:
   an annular race continuously communicating along the circumference of said chamber at one end and receiving said sampled fluid at the tangential velocity;
   a magnetic element contained within said race and formed to be carried by the fluid at the tangential velocity of the sampled fluid;
   detector means externally mounted on said housing for providing an electric pulse with each revolution of said ball; and
   comparator means for comparing the detected pulse frequency with a reference pulse frequency and producing said error signal.

3. A fluid density compensator according to claim 2 wherein said comparator means further comprises:
   a frequency modulator for generating a frequency signal in accordance with the tangential velocity;
   a frequency generator for producing said reference pulse frequency; and
   a frequency comparator for producing said error signal.

4. A density compensated fuel control system for aircraft engines, comprising in combination:
   a main valve for controlling fuel flow to the engine from a pressurized supply;
   regulator means operatively connected to said supply for continuously sampling a portion of the fuel to said main valve;
   a non-magnetic housing forming a short cylindrical chamber and tangentially receiving the sampled fuel at an outer radius and axially discharging the fluid at an inner radius;
   an electromagnetic means operatively connected to said housing for producing an error signal indicative of change in the tangential velocity of the sampled fuel at the outer radius, said error signal controlling the amount of fuel sampled by said regulator means; and
   pressure differential means operatively connected to said housing for measuring the static pressure gradient at the inner and outer radii and producing an output signal to the control system indicative of the fluid density.

5. A fuel control system according to claim 2 wherein said comparator means further comprises:

a frequency modulator for generating a frequency signal in accordance with the tangential velocity;

a frequency generator for producing said reference pulse frequency; and a frequency comparator for producing said error signal.

6. A fuel control system according to claim 1 wherein said electromagnetic means further comprises:

an annular race continuously communicating along the circumference of said chamber at one end and receiving said sampled fuel at the tangential velocity;

a magnetic element contained within said race and formed to be carried by the fuel at the tangential velocity of the sampled fuel;

detector means externally mounted on said housing for providing an electric pulse with each revolution of said ball; and comparator means for comparing the detected pulse frequency with a reference pulse frequency and producing said error signal.